(12) United States Patent
Kuhrts

(10) Patent No.: US 6,475,530 B1
(45) Date of Patent: Nov. 5, 2002

(54) METHODS AND COMPOSITIONS FOR PRODUCING WEIGHT LOSS

(76) Inventor: Eric H. Kuhrts, P.O. Box 387, 1109 Tannery Creek Rd., Bodega, CA (US) 94922

( * ) Notice: Subject to any disclaimer, the term of this patent is extended or adjusted under 35 U.S.C. 154(b) by 0 days.

(21) Appl. No.: 09/684,697

(22) Filed: Oct. 4, 2000

Related U.S. Application Data

(63) Continuation of application No. 09/588,106, filed on May 31, 2000.
(51) Int. Cl.⁷ .................. A01N 65/00; A61K 35/78; A61K 31/74
(52) U.S. Cl. ..................... 424/725; 424/78.01
(58) Field of Search .................. 424/725, 766, 424/78.05, 78.01

(56) References Cited

U.S. PATENT DOCUMENTS 5,055,460 A  * 10/1991  Friedlander ............... 514/161

OTHER PUBLICATIONS

Lane, N. Pain Management in Osteoarthitis: The Role of Cox–2 Inhibitors, 1997, The Journal of Rheumatology, vol. 24, Supplement 49, pp. 20–24.*

Balch et al. Prescription for Nutritional Healing, 1997, pp. 406–407.*

* cited by examiner

Primary Examiner—Jon P. Weber
Assistant Examiner—Patricia Patten
(74) Attorney, Agent, or Firm—Sheldon & Mak; James W. Collett

(57) ABSTRACT

Dislcosed are methods and compositions for producing weight loss in a mammal by administration of a composition containing a weight loss effective amount of a noradrenaline stimulating compound such as ephedrine, mahuang (a plant source of ephedrine alkaloids), citrus aurantium (bitter orange), synephrine, norephedrine, psuedophedrine, a methylxanthine, such as caffeine or guarana, and a botanical COX inhibitor such as resveratrol polygonum cuspidatum, scutellaria baicalensis, turmeric, curcumin, rosmary, green tea, ocimum sanctum (holy basil), or ginger, instead of an NSAID such as aspirin, and optionally a free fatty acid reducing compound. The thermogenic formula is coupled with a growth hormone stimulating formulation containing L-arginine or L-omithine, L-lysine, and a free fatty acid reducing agent such as nicotinic acid. The thermogenic formula would preferably be administered in the daytime, and the growth hormone producing formula at nighttime. The two compositions form a system of AM and PM weight loss strategy for the therapeutic intervention of obesity.

11 Claims, No Drawings

METHODS AND COMPOSITIONS FOR PRODUCING WEIGHT LOSS

This application is a continuation of my application Ser. No. 09/588,106 filed May 31, 2000.

FIELD OF THE INVENTION

This invention relates to methods and compositions for producing weight loss in mammals.

One of the greatest problems confronting modem society in economically successful countries today is obesity. Unfortunately, obesity brings with it the conditions that are ripe for the more serious disease of diabetes.

Among the many possible solutions for treating obesity are formulations of weight loss products that work with some of the basic biochemical processes involved in fat metabolism. This process has been exploited through pharmaceutical intervention at the neurocrine level as well as at the level of fat cells themselves, or the way fat cells metabolize fats in brown adipose tissue.

The term thermogenisis has been coined to describe the process whereby food intake is converted to body heat through the metabolic process of caloric conversion. In obese people, certain metabolic defects associated with the thermogenic process begin to appear. These metabolic predispositions manifest in a number of identifiable biochemical syndromes that can be attacked through therapeutic intervention with agents that over-ride the cascade of events leading to obesity.

One of the more natural approaches to starting artificial thermogenisis, that is, thermogenisis that is unrelated to food consumption, is the use of plant derived substances that contain ephredine or ephedrine like compounds such as ma-haung or ephedra. Ephedra is an herb that grows wild in parts of the western United States. Ephedra contains ephedrine, an alkaloid that stimulates the production of catecholamines such as norepinephrine. Norepinephrine or noradrenaline is presumed to start the thermogenic process by stimulating metabolism in fat cells via the neurocrine axis that involves beta-adrenergic receptors. This in turn results in lipolysis, or the liberation of fat in fat cells via an increase in the basal metabolic rate. This pharmacological intervention results in weight loss in lean, obese, and post-obese human subjects and has been demonstrated in clinical studies (Dulloo, A G & Miller D S, Wrld Rev Nutr Diet 50: 1–56 ;1987).

Ephedra (also known by its Chinese name, MaHuang) has also been combined with methylxanthines such as caffeine, and the prostaglandin inhibitor aspirin, in a three component weight loss formula (U.S. Pat. No. 5055460). Caffeine and aspirin have been shown to potentiate the thermogenic action of ephedrine (Dulloo A. G., Intl. Jour. Obes.; 1993, 17 (Suppl. 1), S35–S40). An increase in catecholamine release as a result of pharmacological intervention with thermogenic agents leads to a blunted response on metabolism because of negative feedback systems associated with biochemical phenomena that take place in the synaptic junction. These negative feedback control systems involve adenosine, free fatty acids, and prostaglandins. The methylxanthines such as caffeine work to overcome the negative feedback related to adenosine, and the aspirin inhibits cyclooxygenase, the enzyme responsible for synthesizing prostaglandins, and a new element has been added in the instant invention by the optional inclusion of nicotinic acid to lower free fatty acids. By inhibiting these negative feedback controls, the thermogenic or up-regulated metabolic effect produced by exogenous administration of agents capable of increasing nor-adrenaline can be potentiated.

One example of the magnitude of potentiation that can be achieved by combining a nor-adrenaline increasing agent such as ephedra, with a prostaglandin inhibitor such as aspirin to reduce feedback inhibition is the study conducted by Dulloo and Miller (Am J Clin Nutr 1987;45:564–9). In this study, aspirin and ephedra together more than doubled the weight loss in mice when compared to the effect of ephedra alone. Aspirin by itself resulted in no weight loss. Ephedra alone resulted in reduced body fat and weight and reduced obesity, but did not reverse obesity, whereas aspirin and ephedra together actually reversed obesity.

The use of aspirin to inhibit cyclooxygenase and thereby reduce prostaglandins is believed to be the mechanism of action that explains its anti-inflammnatory activity. Aspirin is one of the class of compounds known as non-steroidal anti-inflammatory drugs, otherwise known as NSAIDs. These drugs work by inhibiting cyclooxygenase 1, the enzyme that synthesis prostaglandins from arachidonic acid. Prostaglandin E-2 is a pro-inflammatory prostaglandin. But a single large dose of aspirin only inhibits cyclooxygenase partially, but not completely. Prostaglandin levels return to baseline levels within the next 6 hours. In U.S. Pat. No. 5055460, the preferred range for the dose of aspirin is from 200–1000 mg., with the particularly preferred unit dose being 300 mg. of aspirin. This amount of aspirin, with caffeine, and ephedra, is recommended to be taken 1–6 times per day. Yet even a single dose of 300 mg. per day of aspirin is capable of causing gastric erosion in healthy young adults in 5–7 days. Even more serious gastric bleeding would occur if up to six doses per day of this amount of aspirin were to be consumed. The use of aspirin to potentiate the thermogenic effects of ephedra or any other nor-adrenaline, catacholamine stimulating compound is therefore dangerous.

There is a definite need for a safer thermogenic triad that can inhibit the negative feedback produced by prostaglandins, without the side-effects of gastric erosion produced by the NSAID drugs like aspirin. There is also a need for a prostaglandin inhibitor formula that is more effective at suppressing cyclooxygenase and reducing prostaglandins with a single dose, and provide long term reduction of prostaglandins over an 8–24 hour period. There is also a need for a prolonged activity thermogenic formula that increases metabolism all day from a single dose, while at the same time prostaglandin's are being suppressed in parallel over the same time period. There is also a need for a more complete suppression of the negative feedback produced by catecholamine stimulated free fatty acid release.

One attempt to over come the side-effects associated with the use of aspirin in the thermogenic triad has been to substitute white willow bark, which contains salicylic acid, for the aspirin component. Chemically, aspirin is acetylsalicylic acid, which is effective at inhibiting cyclooxygenase, and thereby lowers prostaglandin levels, whereas salicylic acid or white willow bark minimally effective at inhibiting cyclooxygenase, and therefore is not as effective as aspirin at potentiating the thermogenic effects of compounds such as ephedra.

A much safer and more effective composition for the thermogenic triad would be the use of a COX inhibitor other than aspirin. COX-2, or cyclooxygenase-2 inhibitors inhibit cyclooxygenase and reduce prostaglandins without producing the degree of gastric erosion associated with NSAID drugs such as aspirin. However, many COX-2 inhibitors have a short half-life, and do not keep prostagladins suppressed completely or in a prolonged fashion over a 6–24 hour period. In addition, the turnover rate for cyclooxygenase is fairly short.

Another attempt to formulate a weight loss product is described in U.S. Pat. No. 5798101. This patent is directed to herbal compositions to reduce weight and help suppress appetite consisting of St. John's Wort and ephedra with or without caffeine. These formulations do not include a prostaglandin inhibitor such as aspirin or a COX-2 inhibitor, so the thermogenic component (the ephedra) would be less effective at driving metabolism because of the negative feedback from prostaglandins. The St John's Wort is present to produce an effect on serotonin, a neurotransmitter involved in mood and carbohydrate craving. Thus, its function in the formulations described in this patent is as an appetite suppressant, not as a component in the thermogenic triad of ephedra, aspirin, and caffeine.

Growth hormone (GH) has been implicated in a number of metabolic effects. Administration of exogenous growth hormone by injection has been shown to accelerate body fat loss, and produce anabolic effects in obese human subjects (Kim et al, Horm Res 1999;51:78–84). Growth hormone secretion is regulated by two hypothalamic neurohormones; growth hormone releasing hormone (GHRH) and somatostatin (SRIH). GHRH stimulates growth hormone while SRIH has a inhibiting influence. Insulin like growth factor I (IGF-1), mediates the biological actions of growth hormone through negative feedback. A number of nutritional, dietary, and metabolic factors influence the growth hormone-insulin-like growth factor (GH-IGF I) interaction. Insulin levels are elevated in obesity, and high insulin levels also suppress growth hormone production.

Obese people have a blunted or suppressed GH release, even when subjected to growth hormone injections or other nutritional components that have an effect on growth hormone release in normal healthy subjects. Obese people have high levels of circulating free fatty acids (FFA), and free fatty acids have been shown to suppress growth hormone release (J Clin Endocrinol Metab 84: 1234–1238, 1999). Plasma free fatty acids and triglycerides can be reduced by oral administration of nicotinic acid, or esters, analogues, or pro-drugs of nicotinic acid such as 5-methylpyrazinecarboxylic acid 4-oxide (Acipimox, Pharmacia-Upjohn), beta-pyridylcarbinol, mesoinositolhexanicotinate, xantinol nicotinate (Eur. J. Clin. Pharmacol. 16, 11–15, 1979, and Med Sci. Sports Exerc., Vol. 27, No. 7; 1057–1062, 1995).

Surprisingly significant differences exist in the magnitude and duration of plasma free fatty acid reduction from nicotinic acid and its esters, prodrugs, or analogues when the drug is given during the daytime versus the nighttime. If nicotinic acid (niacin) is given in the daytime, it reduces free fatty acids temporarily, but then there is a rebound effect. If given nocturnally, as a constant infusion at night from 8:00 PM to 6 AM, nicotinic acid and its complexes produces a 24 hour reduction in free fatty acids, without the rebound effect. This is particularly important for diabetics and people with type IV hyperlipoproteinemia, who experience a significant rise in triglycerides during the day as a result of a high carbohydrate diet. A slow-release formulation of nicotinic acid or like compound, if taken at night, will cause a dramatic reduction in 24 hour free fatty acid and/or triglyceride levels, and these will remain lowered for at least 24 hours until the next nocturnal dose is taken the following evening.

Growth hormone causes lypolysis, which results in an increase in circulating free fatty acids in plasma. This increase in free fatty acids produces a negative feedback inhibition of growth hormone production. But because free fatty acids are already elevated in obesity, obese individuals have this characteristic blunted basal growth hormone production, as well as when subjected to exogenous growth hormone injections. Elderly subjects also show suppressed spontaneous GH release, and reduced response to growth hormone stimulating agents.

L-arginine is an amino acid that has a pronounced effect on growth hormone and insulin-like growth factor-1. Oral administration of L-arginine can increase growth hormone production in normal non-obese subjects, but less so in obese subjects. In healthy postmenopausal women, 9 grams of L-arginine per day increased growth hormone by 72% (J. Lab Clin Med;135: 231–7; 2000). L-arginie stimulates growth hormone production in obese individuals, but is blunted by the negative feedback produced by high levels of circulating free fatty acids. Pharmacological reduction of free fatty acids in conjunction with injections of growth hormone releasing hormone (GHRH), helps to overcome the suppression of growth hormone in obese and elderly subjects (J Clin Endocrinol Metab, 81:3998–4001, 1996).

The amount of L-arginine needed to stimulate growth hormone secretion is fairly large, usually greater than 500 mg. To get a significant increase in growth hormone production, most studies have employed daily doses above 3 grams, and in many cases 9–30 grams. Since L-arginine is not an inexpensive substance, it would be of great advantage to be able to reduce the dose of L-arginine, and still stimulate significant increases in growth hormone. It has now been found that this is possible by incorporating lower doses of L-argie with the amino acid L-lysine, and a free fatty acid lowering substance such as nicotinic acid.

Free fatty acids follow a diurnal rhythm. During the daytime, when carbohydrates are being consumed, lipolysis is inhibited by insulin, and the free fatty acid level is low. At nighttime, while sleeping, carbohydrates are not being consumed, and consequently free fatty acids are elevated. High free fatty acids at night inhibit growth hormone production, particularly in obese people, and obese subjects have higher levels of circulating free fatty acids than non-obese subjects. Furthermore, catecholamines such as noradrenaline, stimulate free fatty acid release which inhibits lipolysis in adipose or fat cells. Compounds such as ephedra stimulate catecholamine production during thermogenisis, which in turn elevates free fatty acids. The free fatty acids thus serve as negative feedback for fat metabolism (lipolysis), much like the prostaglandins and adenosine previously described. Therefore, there is also a need to keep free fatty acids suppressed during the daytime, when the thermogenic components are ingested.

SUMMARY OF THE INVENTION

It is the object of the present invention to provide safer and more effective weight-loss compositions that combine the anti-obesity properties of two types of metabolic formulations that involve different biochemical aspects. The first compositions, designed to be taken during the day-time (AM component), and preferably in the morning, consist of new and improved thermogenic formulations. The second compositions, which should preferably be taken at night-time (PM component) consist of growth hormone stimulating substances. By stimulating thermogenesis during the day time to metabolize fat, and stimulating more effective growth hormone production at night, and mobilizing fat, a dual action, or two pronged attack, is directed at weight reduction. This takes advantage of a 24 hour biochemical strategy that marshals the best functionality from two of the most well documented weight loss systems currently studied.

The clinical efficacy of the thermogenic triad consisting of (1) a nor-adrenaline stimulating agent such as ephedra, (2) aspirin to inhibit prostaglandins, and (3) the methylxanthine, caffeine, has been well documented in numerous medical journals, but the safety of the aspirin component is a real issue. Furthermore, side-effects from the ephedra are directly related to a spiking of blood levels, or too rapid release. The same problem exists with the caffeine component. Jitteryness, nervousness, and heart palpitations are commonly experienced side-effects associated with high doses and rapid absorption of ephedra and caffeine. Botainical sources of caffeine include guarana (paullinia cupana), and mate (ilex paraguariensis), plants that grow in South America, and green tea, cola nuts, coffee, and cocao. Nicotinic acid has not been previously used as part of any thermogenic strategy. The efficacy of growth hormone treatment in pharmacological intervention of obesity has been hampered by the blunted response to injections of OHRH, and the lower basal production that occurs in obese people. Nevertheless, the association between growth hormone and obesity has been well documented.

It is a further advantage of the invention contained herein to describe side-effect reducing thermogenic formulations that could be consumed by obese individuals for prolonged periods of time without the fear of gastric erosion. Still another benefit is the prolonged activity of the sustained-release formulations that avoid any spiking of blood levels. Yet still another advantage is to provide a more effective growth hormone stimulating composition that more effectively increases growth hormone production in obese individuals as well as elderly and normal healthy subjects. Furthermore, the growth hormone stimulating compositions described herein over come the blunted response to growth hormone stimulation in obese people due to suppression by free fatty acids. This invention also provides for growth hormone formulations that are more effective with lower doses of the amino acid L-arginine, through the inclusion of L-lysine, and a free fatty acid reducing substance such as nicotinic acid. Lastly, the optional inclusion of nicotinic acid into the thermogenic compositions provides for more effective suppression of catecholamine induced negative feedback from free fatty acid release. By combining the metabolic enhancing formulations during the daytime with the growth hormone releasing formulations during the nighttime, a 24 hour formulation strategy is provided that is more effective than either formulation alone, or any individual component alone.

DETAILED DESCRIPTION OF THE INVENTION

The present invention is directed to compositions of noradrenaline stimulating agents such as ephedra, citrus aurentium, or other botanical source of adrenaline stimulating alkaloids, a botanical COX inhibitor such as resveratrol contained in polygonum cuspidatum, and a methyl-xanthine such as caffeine, or a botanical source of caffeine, that inhibits adenosine, and therefore overcomes feedback inhibition of catecholamine release, and optionally, a free fatty acid reducing compound such as nicotinic acid or an analog, or ester of nicotinic acid, This thermogenic formula is coupled with a more effective growth hormone stimulating composition of L-arginine and L-lysine or L-ornithine and L-lysine and nicotinic acid, or analogs, or esters of nicotinic acid such as inositol-hexanicotinate, 5 methylpyrazinecarboxylic acid 4 oxide (Acipimox), xantinol nicotinate, pyridylcarbinol, or arginine nicotinate.

Salts, esters, peptides,derivatives, or complexes of L-arginine and L-lysine or L-ornithine and L-lysine may be used for the growth hormone stimulating agent, and any free fatty acid reducing agent may be used for the nicotinic acid component. Long acting preparations of nicotinic acid are preferred, particularly, sustained-release formulations, so that they can be administered at night, to keep 24 hour free fatty acids reduced. Ideally, these long acting preparations would release the niacin from about 6:00 PM to 6:00 AM, or about 12 hours.

The thermogenic formula would stimulate metabolism and produce lypolysis during the daytime when people are active, and the growth hormone stimulating compositions would be taken at night, when carbohydrate consumption and insulin are at a minimum, and free fatty acids are at their peak.

In its broadest sense, the present invention is directed to a method for producing weight loss in a mammal by administering a composition containing a weight loss effective amount of a noradrenaline stimulating compound such as ephedrine, mahuang (a plant source of ephedrine alkaloids), *citrus aurantium* (bitter orange), synephrine, norephedrine, psuedophedrine, a methylxanthine, such as caffeine or guarana, and a COX-2 inhibitor such as resveratrol, *polygonum cuspidatum, scutellaria baicalensis*, white willow bark, turmeric, curcumin, rosmary, green tea, *ocimum sanctum* (holy basil), or ginger, instead of an NSAID such as aspirin. The preferred COX-2 inhibitor would be resveratrol from a botanical source such as *polygonum cuspidatum* or *polygonum multiflorum*.

*Polygonum cuspidatum*, a member of the buckwheat family (polygonaceae), commonly known as japanese knotweed. This plant is a native of eastern Asia, but also grows wild throughout northeastern America and southern Canada. The roots *Polygonum cuspidatum* contain a large amount of resveratrol, a stilbene which is a powerful anti-oxidant, and exhibits anti-inflammatory, anti-mutagen, and anti-carcinogenic properties. Resveratrol also inhibits blood platelet aggregation, making it a beneficial cardiovascular compound. Recently, resveratrol was found to inhibit COX-2 by dose dependently reducing prostaglandin,E-2 (PGE2) production in human mammary epithelial cells. The dried roots of *Polygonum cuspidatum* contain about 5–8% resveratrol. By using various extracting techniques to concentrate the amount of resveratrol in *Polygonum cuspidatum*, high yield powders have been obtained that contain up to 20% resveratrol. Therefore, 100 mg. of Polygonum cuspidatum extract will deliver 20 mg. of actual resveratrol. Synthetic resveratrol is available, but it is extremely expensive, about $250.00 per gram.

Other plant sources of resveratrol include grapes or wine (Vitus vinfera), which contains 1–13 mg. of resveratrol per liter, with an average of about 5 mg./liter. Clearly a safer and higher yielding source of resveratrol is *Polygonum cuspidatum*, since fairly large amounts can be obtained in pill form with the concentrated extract.

Resveratrol is also present in the following plants; *Polygonum multiflorum, Pterolobium hexapetallum, Cassia garrettiana Carib, Cassia quinquangulata, Arachis hypogaea, Eucalyptus globulus*, and *Bauhinia racemosa Lamk, Veratrum grandiflorum*, and *Veratrum formosanum*.

While resveratrol is perhaps the most widely studied of the constituents in *Polygonum cuspidatum*, there are also other active substances contained therein, such as emodin, polydatin, and piceid. These may contribute to the beneficial effects of the plant extract in a synergistic fashion, but also exhibit some of the same and other pharmacological properties as resveratrol.

In general, the amount of ephedrine would be about 20–350 mg. per day, preferably about 25–100 mg. per day. The amount of caffeine or caffeine containing botanical yielding 10–500 mg./day, preferably about 20–200 mg./day. The amount of resveratrol or botanical source of resveratrol would yield from 1–500 mg. per day of actual resveratrol. Other COX-2 inhibitors must be used at a level that significantly inhibits the COX-2 enzyme, or enough to reduce prostaglandin synthesis sufficient to overcome feedback inhibition of the thermogenisis initiated by the noradrenaline stimulating agent. Nicotinic acid or analogues, esters, or pro-drugs of nicotininc acid may optionally be added to the thermogenic daytime formula. The components in the thermogenic triad may be in immediate-release form or sustained-release form. The ingredients are preferably in sustained-release form as this prolongs the metabolic activity and reduces the potential for side-effects that may arise from "spiking" or a rapid rise in blood levels of the respective compounds if given in immediate-release form.

The instant invention also includes a growth hormone producing combination of L-arginine or L-ornithine with L-lysine and nicotinic acid (niacin) in a separate dosage form that could be taken at night, or the arginine/lysine combination and niacin could be taken at the same time as the thermogenic formula. The daily dose or nightly dose of arginine and lysine (the dose that would be taken during any 24 hour period) would be from 50 mg. to 30 grams of each amino acid. The daily or nightly (24 hour) dose of niacin would be from 50 mg. to 3 grams. The preferable dose would be about 1.2 grams of L-arginine, 1.2 grams of L-lysine, and 200 to 750 mg. of niacin (nicotinic acid). The same amounts of omithine could be substituted for the arginine. The arginine or ornithine, lysine, and niacin may be in immediate-release form or sustained-release form, but preferably in sustained-release form. The preferred time for administration would be at nighttime.

Alternatively, an ester of arginine or lysine and nicotinic acid could be used for the growth hormone stimulating formulation. Such an ester is arginine nicotinate as described in U.S.Pat. No. 5157022. Likewise, an arginine derivitive compound such as arginine aspartate, arginine alpha ketogluterate, or a di-peptide of arginine such as alanylarginine (ALA-ARG), valinyl-arginine (VAL-ARG), or leucinyl-arginine (LEU-ARG) can be used with L-lysine and the nicotinic acid component. Or tri-peptides containing arginine such as argininyl-lysinyl-glutamic acid (ARG-LYS-GLU) and arginyl-glysyl-arginine (ARG-GLY-ARG) can be combined with L-lysine and nicotinic acid.

As mentioned above, any of these arginine, lysine, or ornithine, derivative compounds or salts can be combined with esters or pro-drugs of nicotinic acid such as acipimox, beta-pyridylcarbinol, mesoinositol-hexanicotinate, xantinol nicotinate or other like compounds or derivatives of nicotinic acid.

Furthermore, recombinant human growth hormone or bovine growth hormone, both of which must be injected, can be used in conjunction with L-lysine and nicotinic acid or its esters or prodrugs such as arginine nicotinate, to enhance weight loss in obese subjects. However, the preferable route of administration would be oral, the composition; L-arginine hydrochloride, L-lysine hydrochloride, and nicotinic acid, and in sustained-release form.

Useful dosage forms include without limitation oral forms such as tablets, capsules, beads, granules, aggregates, powders, gels, liquids, solids, semi-solids, and suspensions. Lotions, transdermal delivery systems, including dermal patches, aerosols or nasal mists, suppositories, salves and ointments are also useful.

A variety of additives can be incorporated into the inventive compositions for their intended functions. These additives are usually used in small amounts.

Useful additives include, for example, gelatin, vegetable proteins such as sunflower protein, soybean proteins, cotton seed proteins, peanut proteins, rape seed proteins, blood proteins, egg proteins, acrylated proteins; water-soluble polysaccharides such as alginates, carrageenans, guar gum, agar-agar, gum arabic, and related gums (gum ghatti gum karaya, gum tragacanth), pectin; water-soluble derivatives of cellulose: alkylcelluloses, hydroxyalkylcelluloses and hydroxyalkylalkylcelluloses, such as methylcellulose, hydroxymethylcellulose, hydroxyethylcellulose, hydroxypropylcellulose, hydroxyethylmethylcellulose, hydroxpropylmethylceflulose, hydroxbutylmethylcellulose, cellulose esters and hydroxyalkylcellulose esters such as: cellulose acetate phthalate (CAP), carboxyalky I celluloses, carboxyalkylalkylcelluloses, carboxyalkylcellulose esters such as carboxymethyl cellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVP/vinyI acetate copolymer, and polycrotonic acids; also suitable are phthalated gelatin, gelatin succinate, crosslinked gelatin, shellac, water-soluble chemical derivatives of starch, cationically modified acrylates and methacrylates possessing, for example, a tertiary or quaternary amino group, such as the diethylan-finoethyl group, which may be quatemized if desired; and other similar polymers.

Processing aids such as sucrose, polydextrose, maltodextrin, lactose, maltose, stearic acid, microcrystalline cellulose, and the like may also be used. Examples of classes of additives include excipients, lubricants, oils, hydrocolloid suspending agents, buffering agents, disintegrating agents, stabilizers, foaming agents, pigments, coloring agents, fillers, bulking agents, sweetening agents, flavoring agents, fragrances, release modifiers, ect.

Sustained release within the scope of this invention can be taken to mean any one of a number of extended release dosage forms. The following terms may be considered to be substantially equivalent to sustained release, for the purposes of the present invention: continuous release, sustained release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski *Extended-Release Dosage Forms,* 1987 (CRC Press, Inc.).

The various sustained release technologies cover a very broad spectrum of drug dosage forms. Sustained release technologies include, but are not limited to physical systems and chemical systems. Physical systems include, but not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., non-erodible, erodible, environmental agent ingression, and degradable), and materials physically dispersed in non-porous, polymeric, or elastomeric matrices (e.g., non-erodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous).

Hydrogels may also be employed as described in "Controlled Release Systems: Fabrication Technology", Vol. 11, Chapter 3; p 41–60; "Gels For Drug Delivery", Edited By Hsieh, D.

Sustained release drug delivery systems may also be categorized under their basic technology areas, including, but not limited to, rate-preprogrammed drug delivery systems, activation-modulated drug delivery systems, feedback-regulated drug delivery systems, and site-targeting drug delivery systems.

Furthermore, compositions according to the invention may be administered or coadministered with conventional pharmaceutical binders, excipients and additives. Many of these are sustained-release polymers which can be used in sufficient quantities to produce a sustained-release effect. These include, but are not limited to, gelatin, natural sugars such as raw sugar or lactose, lecithin, mucilage, plant gums, pectin's or pectin derivatives, algal polysaccharides, glucomannan, agar and lignin, guar gum, locust bean gum, acacia gum, xanthan gum, carrageenan gum, karaya gum, tragacanth gum, ghatti gum, starches (for example corn starch or amylose), dextran, polyvinyl pyrrolidone, polyvinyl acetate, gum arabic, alginic acid, tylose, talcum, lycopodium, silica gel (for example colloidal), cellulose and cellulose derivatives (for example cellulose ethers, cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate, cross-linked sodium carboxymethylcellulose, cross-linked hydroxypropylcellulose, high-molecular weight hydroxymethylpropcellulose, carboxymethyl-cellulose, low-molecular weight hydroxypropylmethylcellulose medium-viscosity hydroxypropylmethylcellulose hydroxyethylcellulose, hydroxypropylcellulose, hydroxypropylmethylcellulose, sodium carboxymethylcelulose, alkylcelluloses, ethyl cellulose, cellulose acetate, cellulose propionate (lower, medium or higher molecular weight), cellulose acetate propionate, cellulose acetate butyrate, cellulose triacetate, methyl cellulose, hydroxypropyl cellulose, or hydroxypropylmethyl cellulose), fatty acids as well as magnesium, calcium or aluminum salts of fatty acids with 12 to 22 carbon atoms, in particular saturated (for example stearates such as magnesium stearate), polycarboxylic acids, emulsifiers, oils and fats, in particular vegetable (for example, peanut oil, castor oil, olive oil, sesame oil, cottonseed oil, corn oil, wheat germ oil, sunflower seed oil cod liver oil, or high melting point hydrogenated vegetable oil such as can be produced from soy beans); glycerol esters and polyglycerol esters of saturated fatty acids $C_{12}H_{24}O_2$ to $C_{18}J_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10–18 carbon atoms) with monovalent aliphatic alcohols (1 to 20 carbon atoms) or multivalent alcohols such as glycols, glycerol diethylene glycol pentacrythritol, sorbitol mannitol and the like, which may optionally also be etherified, esters of citric acid with primary alcohols, acetic acid, urea, benzyl benzoate, dioxolanes, glyceroformals, tetrahydrofurfuryl alcohol polyglycol ethers with $C_1$–$C_{12}$-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

EXAMPLE 1

AM Weight Loss Formulation
Each tablet contains:

| | |
|---|---|
| Ephedra SR (6% alkaloids, 12 mg. ephedrine) | 200 mg.* |
| Guarana | 300 mg |
| Polygonum cuspidatum (15% Resveratrol) | 200 mg. |
| Dicalcium Phosphate Anhydrous | 150 mg. |
| Microcrystalline cellulose | 50 mg. |
| Steric acid 92% | 12 mg. |
| Magnesium Stearate | 10 mg. |

*The ephedra (Ma Huang) powder can be processed as a sustained-release powder using standard techniques known to the pharmaceutical industry.

PM Weight Loss Formulation
Each Tablet Contains:

| | |
|---|---|
| L-arginine HCL | 350 mg |
| L-lysine HCL | 350 mg.. |
| Niacin SR | 250 mg.* |
| Dicalcium phosphate (anhydrous) | 150 mg. |
| MCC 102 | 50 mg.** |
| Stearic acid 92% | 12 mg. |
| Mg St. | 5 mg. |

*The niacin is processed as a sustained-release powder that is incorporated into the tablet with the other ingredients.
**microcrystalline cellulose This formula would be a four tablet dose, each dose delivering about 1,200 mg. of L-arginine, 1,200 mg. of L-lysine, and 500 mg. of niacin.

The daytime or AM formula metabolizes fat by utilizing the thermogenic mechanism, while the PM formulation mobilizes fat, lowers free fatty acids, and increases production of growth hormone by overcoming the suppression of growth hormone by high free fatty acids in overweight individuals. When taken together over a 24 hour period, the two formulas result in more effective weight loss.

All of the ingredients in the above formulas may also be sustained-release, or immediate-release, or a combination of sustained-release and immediate-release such as indicated in the examples.

EXAMPLE 2
Growth Hormone Stimulating Weight Loss Formulation

L-arginine free base, L-lysine HCL, hydrogenated vegetable oil, and niacin are processed in a high shear mixer that is jacketed so as to allow high temperature water to be circulated and maintained around the vessel. The three ingredients are mixed together at a temperature of about 150° F. until the oil melts and mixes thoroughly with the niacin, L-lysine, and L-arginine. The unit is then cooled and the powder discharged. In this way, a free flowing sustained-release powder is produced containing 98% of the arginine, lysine, and niacin amounts indicated below. This powder is then blended into the final powdered drink mix that follows; Each serving contains;

| | | |
|---|---|---|
| L-arginine free base | 1.5 grams | (sustained-release) |
| L-lysine HCL | 1.5 grams | (sustained-release) |
| Niacin | 0.5 grams | (sustained-release) |
| Maltodextrin | 5 grams | |
| Citric acid | 2 grams | |
| Guar gum | 0.2 grams | |
| Lemon lime flavor | 0.15 grams | |
| Sucralose | 0.030 grams | |
| Yellow #5 | 0.25 grams | |

The above drink mix is a pleasant tasting powder that can be taken in the evening, and releases the niacin and arginine all night while the subject is asleep. The result is significant growth hormone production and free fatty acid reduction, which contributes to weight loss and reduction of body flat.

EXAMPLE 3
Growth Hormone Nighttime formula
Each tablet contains:

| | |
|---|---|
| Acipimox (Pharmacia Upjohn) | 50 mg.* |
| L-arginine HCL | 350 mg |
| L-lysine HCL | 350 mg.. |
| Guar Gum | 150 mg. |
| Microcrystalline cellulose | 50 mg. |
| Lactose anhydrous | 25 mg. |
| Stearic acid (92%) | 15 mg. |
| Magnesium stearate | 5 mg. |

*5-methylpyrazinecarboxylic acid 4-oxide

The above formulation is designed to be taken as a 4 tablet dose, at about 6:00 PM, which would deliver about 1.2 grams of L-arginine, 1.2 grams of L-lysine, and 200 mg. of acipimox per evening while the subject is asleep.

Example 4
Arginine Derivative Growth Hormone Stimulating Weight Loss Formula Arginine nicotinate is prepared as described in U.S. Pat. No. 5157022 and was formulated into a pleasant tasting drink mix that delivers 5 grams of arginine nicotinate per serving:

| | |
|---|---|
| Arginine nicotinate | 5 grams |
| L-lysine HCL | 1.5 grams |
| Maltodextrin | 3 grams |
| Citric acid | 2 grams |
| Guar gum | 0.2 grams |
| Lemon lime flavor | 0.15 grams |
| Sucralose | 0.030 grams |
| Yellow #5 | 0.25 grams |

The above powder is designed to be mixed in water or juice and consumed at about 6:00 PM in the evening. The result is significant reduction in 24-hour free fatty acid levels with a concomitant increase in growth hormone production and reduction in obesity.

EXAMPLE 5
Thermogenic Formula with Nicotinic Acid
Each tablet contains:

| | |
|---|---|
| MaHuang (8% ephedrine alkaloids) | 200 mg. |
| Guarana | 300 mg |
| Polygonum cuspidatum (15% Resveratrol) | 100 mg. |
| Nicotinic acid (sustained-release) | 250 mg. |
| Dicalcium Phosphate Anhydrous | 150 mg. |
| Microcrystalline cellulose | 50 mg. |
| Stearic acid 92% | 12 mg. |
| Magnesium Stearate | 5 mg. |

The formula of example 5 employs sustained-release niacin or nicotinic acid, and the nicotinic acid helps to overcome the negative feedback produced by the MaHuang which stimulates catecholamine (noradrenaline) release which in turn leads to release of free fatty acids that inhibit lipolysis and blunts the thermogenic effects. The formula of the above example 5 can be combined with the PM or nighttime formula of any of the other examples of growth hormone inducing formulas listed above in any 24 hour period.

What is claimed is:

1. A weight loss composition comprising:
   a thermogenic noradrenaline generating substance containing at least one compound selected from the group consisting of ephedrine, synephrine and pharmaceutically acceptable salts thereof;
   a COX-2 inhibitor; and
   a methylxanthine.

2. The composition of claim 1, wherein the COX-2 inhibitor is derived from a botanical.

3. The composition of claim 2, wherein the botanical is selected from the group consisting of *Polygonum cuspidatum*, *Polygonum multiflorum*, *Scutellaria baicalensis*, white willow bark, turmeric, curcumin, rosemary, green tea, *Ocimum sanctum* (holy basil), and ginger.

4. The composition of claim 1, further comprising nicotinic acid.

5. The composition of claim 1, wherein the COX-2 inhibitor is resveratrol that is derived from *Polygonum cuspidatum* or *Polygonum multiflorum*.

6. The composition of claim 1, further comprising a free fatty acid reducing compound.

7. The composition of claim 6, wherein the free fatty acid reducing compound is selected from the group consisting of nicotinic acid, arginine nicotinate, and pharmaceutically acceptable salts.

8. The composition of claim 1, wherein the noradrenaline generating compound comprises ephedrine derived from the botanical Ephedra.

9. The composition of claims 1, wherein the noradrenaline generating compound comprises synephrine derived from a citrus botanical.

10. The composition of claim 9, wherein the citrus botanical is *Citrus aurantium*.

11. The composition of claim 1, further comprising a growth hormone producing compound selected from the group consisting of L-arginine, L-lysine and pharmaceutically acceptable salts thereof.

* * * * *